United States Patent
Maurin et al.

(10) Patent No.: US 6,432,894 B1
(45) Date of Patent: *Aug. 13, 2002

(54) COMPOSITION FOR WASHING KERATIN MATERIALS, BASED ON A DETERGENT SURFACTANT, A POLYORGANOSILOXANE AND AN ACRYLIC TERPOLYMER

(75) Inventors: Véronique Maurin, Paris; Bernard Beauquey, Clichy, both of (FR)

(73) Assignee: L'Oreal, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 09/671,195

(22) Filed: Sep. 28, 2000

(30) Foreign Application Priority Data

Sep. 29, 1999 (FR) .............................................. 99 12163

(51) Int. Cl.⁷ .............................. C11D 9/36; C11D 3/37
(52) U.S. Cl. ...................... 510/122; 510/119; 510/121; 510/123; 510/124; 510/125; 510/466; 510/477; 510/318; 510/229
(58) Field of Search ................................ 510/119, 121, 510/122, 123, 124, 125, 466, 477, 318, 229

(56) References Cited

U.S. PATENT DOCUMENTS 5,573,709 A    11/1996 Wells .......................... 510/122

FOREIGN PATENT DOCUMENTS

| EP | 824 914 | * | 2/1998 |
| EP | 824914 | * | 2/1998 |
| EP | 00825 200 | | 2/1998 |
| WO | 94/06403 | * | 3/1994 |

* cited by examiner

Primary Examiner—Charles Boyer
(74) Attorney, Agent, or Firm—Jacobson Holman, PLLC

(57) ABSTRACT

A composition for washing keratin materials, combines, in a cosmetically acceptable medium: i) at least one detergent surfactant; ii) at least one polyorganosiloxane oil with a viscosity greater than or equal to $0.1\ m^2.s^{-1}$; and iii) at least one acrylic terpolymer made up of a monomer (a) chosen from a $C_1$–$C_6$ alkyl acrylate and a $C_1$–$C_6$ alkyl methacrylate, a monomer (b) chosen from a heterocyclic vinyl compound with at least one nitrogen or sulphur atom, a (meth) acrylamide, a mono- or di($C_1$–$C_4$)alkylamino($C_1$–$C_4$)alkyl (meth)acrylate and a mono- or di($C_1$–$C_4$)alkylamino($C_1$–$C_4$) alkyl (meth)acrylamide, and a monomer (c) chosen from a urethane produced by reaction between a monoethylenic unsaturated isocyanate and a nonionic surfactant, a copolymerizable ethylenic surfactant monomer, a surfactant monomer of urea type, an allyl ether carrying alkylenoxy groups and a nonionic monomer of urethane type.

38 Claims, No Drawings

COMPOSITION FOR WASHING KERATIN MATERIALS, BASED ON A DETERGENT SURFACTANT, A POLYORGANOSILOXANE AND AN ACRYLIC TERPOLYMER

The present invention relates in general to compositions for washing keratin materials, based on a detergent surfactant, a polyorganosiloxane of specific viscosity and an acrylic terpolymer, as well as to a washing process using these compositions.

Polyorganosiloxanes are generally used in shampoo compositions as conditioners to improve the softness, feel and disentangling of the hair. However, it has been found that these polyorganosiloxanes lead to the formation of an aesthetically unpleasant layer at the surface of the shampoo, which consumers find undesirable. To avoid the appearance of this phenomenon, stabilizers such as crosslinked arylic polymers of the Carbopol type are often used. However, these stabilizers have the drawback of reducing the cosmetic performance qualities of shampoos, in particular by making the hair more charged and more coarse.

It was thus necessary to develop a detergent cosmetic composition containing polyorganosiloxanes, in particular a shampoo, which has a satisfactory aesthetic appearance while at the same time giving acceptable cosmetic performance qualities to keratin materials, i.e. in particular the hair and the scalp.

The Applicant has discovered, surprisingly, that it is possible to formulate compositions for washings keratin materials, in particular shampoos, which have the desired properties, by using in these compositions a detergent surfactant and a polyorganosiloxane with a viscosity of greater than or equal to $0.1$ $m^2.s^{-1}$ combined with a specific acrylic terpolymer, defined below. Specifically, it has been found that the use of the said acrylic terpolymer in the compositions of the present invention improves the stability of polyorganosiloxane-based shampoos with a viscosity of greater than or equal to $0.1$ $m^2.s^{-1}$ while at the same time giving the hair satisfactory cosmetic properties, and in particular for dried hair more lightness, suppleness, manageability and body. The hair also generally looks smoother.

It has also been found that the compositions of the present invention have good skin tolerance and facilitate the disentangling of dried hair.

A subject of the invention is thus compositions for washing keratin materials, essentially characterized in that they comprise, in a cosmetically acceptable medium:

i) at least one detergent surfactant;
ii) at least one polyorganosiloxane with a viscosity of greater than or equal to $0.1$ $m^2.s^{-1}$; and
iii) at least one acrylic terpolymer consisting of:
   from 5% to 80% by weight, preferably from 15% to 70% by weight and more preferably from 40% to 70% by weight, of an acrylate monomer (a) chosen from a $C_1$–$C_6$ alkyl acrylate and a $C_1$–$C_6$ alkyl methacrylate;
   from 5% to 80% by weight, preferably from 10% to 70% by weight and more preferably from 20% to 60% by weight, of a monomer (b) chosen from a heterocyclic vinyl compound containing at least one nitrogen or sulphur atom, a (meth)acrylamide, a mono- or di($C_1$–$C_4$)alkylamino($C_1$–$C_4$)alkyl (meth)acrylate and a mono- or di($C_1$–$C_4$)alkylamino($C_1$–$C_4$)alkyl(meth)acrylamide;
   from 0.1% to 30% by weight, preferably from 0.1% to 10% by weight, of a monomer (c) chosen from:
   a urethane produced by reaction between a monoethylenic unsaturated isocyanate and a nonionic surfactant encompassing a block copolymer of 1,2-butylene oxide and of ethylene oxide containing a $C_{1-4}$ alkoxy end;
   a copolymerizable ethylenic unsaturated surfactant monomer obtained by condensing a nonionic surfactant with an α,β-ethylenic unsaturated carboxylic acid or its anhydride;
   a surfactant monomer chosen from reaction products such an urea of a monoethylenic unsaturated monoisocyanate with a nonionic surfactant containing an amine function;
   a (meth)allyl ether of formula $CH_2=CR_1CH_2OA_mB_nA_pR_2$ in which $R_1$ denotes a hydrogen atom or a methyl group, A denotes a propylenoxy or butylenoxy group, B denotes ethylenoxy, n is equal to zero or denotes an integer less than or equal to 200 and preferably less than or equal to 100, m and p denote zero or an integer less than n and $R_2$ is a hydrophobic group of at least 8 carbon atoms and preferably of $C_8$–$C_{30}$; and a nonionic monomer such as urethane produced by reaction of a monohydric nonionic surfactant with a monoethylenic unsaturated isocyanate;
   the weight percentages of monomers being based on the total weight of the monomers constituting the terpolymer.

In the washing composition of the invention, the acrylic terpolymer is present in a proportion of from 0.01% to 20% by weight of active material (A.M.), preferably 0.1% to 10% by weight, relative to the total weight of the composition.

Preferred acrylate monomers (a) in particular comprise $C_2$–$C_6$alkyl acrylates. Ethyl acrylate is most particularly preferred.

Examples of preferred monomers (b) which may be mentioned are N,N-dimethylaminoethyl methacrylate (DMAEMA), N,N-diethylaminoethyl acrylate, N,N-diethylaminoethyl methacrylate, N-t-butylaminoethyl acrylate, N-t-butylaminoethyl methacrylate, N,N-dimethylaminopropylacrylamide, N,N-dimethylaminopropylmethacrylamide, N,N-diethylaminopropylacrylamide and N,N-diethylaminopropylmethacrylamide. N,N-dimethylaminoethyl methacrylate is most particularly preferred.

The preferred monomers (c) are the copolymerizable ethylenic unsaturated surfactant monomers obtained by condensing a nonionic surfactant with an α,β-ethylenic unsaturated carboxylic acid or its anhydride, preferably $C_3$–$C_4$ mono- or dicarboxylic acids or their anhydrides and more particularly acrylic acid, methacrylic acid, crotonic acid, maleic acid, maleic anhydride and most particularly itaconic acid and itaconic anhydride.

The monomers (c) that are particularly preferred correspond to the copolymerizable ethylenic unsaturated surfactant monomers obtained by condensing a nonionic surfactant with itaconic acid. Among the nonionic surfactants which may be mentioned in particular are $C_{10}$–$C_{30}$ fatty alcohols alkoxylated with 2 to 100 mol and preferably from 5 to 50 mol of an alkylene oxide, such as, for example, polyethylene glycol ethers of a $C_{10}$–$C_{30}$ fatty alcohols and more particularly the polyethylene glycol ethers of cetyl alcohol which are known as Ceteth in the CTFA dictionary, 7th edition, 1997.

Conventional methods for preparing these acrylic terpolymers are known to those skilled in the art. Such methods include solution polymerization, precipitation polymerization and emulsion polymerization, for example. Terpolymers in accordance with the invention and methods for preparing them are described in particular in patent applications EP-A-0 824 914 and EP-A-0 825 200.

Among these terpolymers, it is preferred in particular to use the <<Structure® Plus>> polymer sold by the company National Starch, which consists of acrylates, amino (meth) acrylates and $C_{10}$–$C_{30}$ alkyl itaconate, polyoxyethylenated with 20 mol of ethylene oxide, in the form of an aqueous dispersion containing 20% A.M.

In addition to these monomers, the terpolymer can contain other monomers which allow the said terpolymer to be crosslinked. These monomers are used in relatively low proportions, of up to 2% by weight relative to the total weight of the monomers used to prepare the terpolymer. Such crosslinking monomers comprise aromatic monomers bearing several vinyl substituents, alicyclic monomers bearing several vinyl substituents, bifunctional esters of phthalic acid, bifunctional esters of methacrylic acid, multifunctional esters of acrylic acid, N-methylenebisacrylamide and aliphatic monomers bearing several vinyl substituents such as dienes, trienes and tetraenes. Crosslinking monomers may be, in particular, divinylbenzenes, trivinylbenzenes, 1,2,4-trivinylcyclohexenes, 1,5-hexadienes, 1,5,9-decatrienes, 1,9-decadienes, 1,5-heptadienes, diallyl phthalates, ethylene glycol dimethacrylate, polyethylene glycol dimethacrylate, penta- and tetraacrylates, triallyl pentaerythritols, octaallyl sucroses, cycloparaffins, cycloolefins and N-methylenebisacryl amide.

The viscosity is preferably measured by capillary viscometry, for example using a capillary viscometer, in particular of the Ubbelohde type at a temperature of 25° C., according to ASTM standard D445-97. The method known as the falling-ball method may also be used.

In the context of the present invention, the expression <<polyorganosiloxanes with a viscosity of greater than or equal to 0.1 $m^2.s^{-1}$>> means:

(i) polyalkylsiloxanes; among the polyalkylsiloxanes which may be mentioned mainly are linear polydimethylsiloxanes containing trimethylsilyl end groups, such as, for example, and in a non-limiting manner, the <<Silbione>> oils of the 70047 series sold by Rhodia Chimie and polydimethylsiloxanes containing hydroxydimethylsilyl end groups;

(ii) polyarylsiloxanes;

(iii) polyalkylarylsiloxanes; mention may be made of linear and branched polymethylphenylsiloxanes, polydimethylmethylphenylsiloxanes and polydimethyldiphenylsiloxanes;

(iv) silicone gums; these are polydiorganosiloxanes with a molecular mass of between 200,000 and 5,000,000, used alone or as a mixture in a solvent chosen from volatile silicones, polydimethylsiloxane (PDMS) oils, polyphenylmethylsiloxane (PPMS) oils, isoparaffins, methylene chloride, pentane, dodecane, tridecane and tetradecane, or mixtures thereof; they can, for example, contain the following structures:
polydimethylsiloxane,
poly[(dimethylsiloxane)/(methylvinylsiloxane)],
poly[(dimethylsiloxane)/(diphenylsiloxane)],
poly[(dimethylsiloxane)/(phenylmethylsiloxane)],
poly[(dimethylsiloxane)/(diphenylsiloxane)/(methylvinylsiloxane)]
mention may also be made, by way of example, and in a non-limiting manner, of the following mixtures:

1) mixtures formed from a polydimethylsiloxane hydroxylated at the end of the chain (Dimethiconol according to the CTFA nomenclature) and from a cyclic polydimethylsiloxane (Cyclomethicone according to the CTFA nomenclature), such as the product <<Q2 1401>> sold by the company Dow Corning;

2) mixtures formed from a polydimethylsiloxane gum with a cyclic silicone, such as the product <<SF 1214 Silicone Fluid>> from General Electric, which is an SE 30 gum of MW 500,000 dissolved in <<SF 1202 Silicone Fluid>> (decamethylcyclopentasiloxane);

3) mixtures of two PDMSs of different viscosity, in particular of a PDMS gum and of a PDMS oil, such as the products <<SF 1236>> and <<CF 1241>> from the company General Electric;

(v) silicone resins; preferably crosslinked siloxane systems containing $R_2SiO_{2/2}$, $RSiO_{3/2}$ and $SiO_{4/2}$ units in which R represents a hydrocarbon group containing 1 to 6 carbon atoms or a phenyl group. Among these resins, mention may be made of the product sold under the name <<Dow Corning 593>>;

(vi) or mixtures thereof.

These silicones can be used as they are or in the form of solutions in organic solvents or alternatively in the form of emulsions or microemulsions.

The preferred polyorganosiloxanes are, in particular, the products belonging to classes i) and iv).

The silicones that are particularly preferred in accordance with the invention are:

silicones chosen from the family of polydimethylsiloxanes containing trimethylsilyl end groups, such as oils with a viscosity of between 0.2 $m^2/s$ and 2.5 $m^2/s$ at 25° C., for instance the oils of the series DC200 from Dow Corning, of the series Silbione® 70047 and 47 and more particularly Silbione® 70 047 V 500,000 oil, which are sold by the company Rhodia Chimie, or the silicone oil AK 300,000 from the company Wacker, and polydimethylsiloxanes containing dimethylsilanol end groups, such as dimethiconols;

mixtures of polyorganosiloxanes and of cyclic silicones, such as the product Q2 1401 sold by the company Dow Corning, and the product SF 1214 sold by the company General Electric;

mixtures of two PDMSs of different viscosities, in particular a gum and an oil, such as the product SF 1236 sold by the company General Electric.

The polyorganosiloxanes with a viscosity of greater than or equal to 0.1 $m^2.s^{-1}$ can be present in proportions of between 0.01% and 20% by weight relative to the total weight of the composition and preferably in proportions of between 0.1% and 10% by weight relative to the total weight of the composition.

As mentioned previously, the compositions according to the invention contain at least one detergent surfactant, chosen in particular from anionic, amphoteric, nonionic and cationic surfactants with detergent properties, and mixtures thereof.

Among the anionic surfactants which may be mentioned are alkaline salts, ammonium salts, amine salts, amino alcohol salts and magnesium salts of the following compounds: alkyl sulphates, alkyl ether sulphates, alkylamido ether sulphates, alkylaryl polyether sulphates, monoglyceride sulphates; alkyl sulphonates, alkylamide sulphonates, alkylaryl sulphonates, olefin sulphonates, paraffin sulphonates; alkyl sulphosuccinates, alkyl ether sulphosuccinates, alkylamide sulphosuccinates; alkyl sulphosuccinamates; alkyl sulphoacetates; alkyl phosphates, alkyl ether phosphates; acyl sarcosinates, acyl isethionates and N-acyl taurates.

The alkyl or acyl radical in these various compounds generally consists of a carbon-based chain containing from 8 to 30 carbon atoms.

Among the anionic surfactants which may also be mentioned are fatty acid salts such as oleic, ricinoleic, palmitic and stearic acid salts; coconut oil acid or hydrogenated coconut oil acid; acyl lactylates, in which the acyl radical contains from 8 to 30 carbon atoms.

Surfactants considered as weakly anionic can also be used, such as polyoxyalkylenated carboxylic alkyl or alkylaryl ether acids or salts thereof, polyoxyalkylenated carboxylic alkylamido ether acids or salts thereof, and alkyl D-galactosiduronic acids or salts thereof.

The nonionic surfactants are chosen more particularly from polyethoxylated, polypropoxylated or polyglycerolated fatty acids or alkylphenols or alcohols, with a fatty chain containing 8 to 30 carbon atoms, the number of ethylene oxide or propylene oxide groups being between 2 and 50 and the number of glycerol groups being between 2 and 30.

Mention may also be made of copolymers of ethylene oxide and propylene oxide; condensates of ethylene oxide and of propylene oxide with fatty alcohols; polyethoxylated fatty amides preferably containing 2 to 30 mol of ethylene oxide; polyglycerolated fatty amides preferably comprising 1 to 5 and in particular 1.5 to 4 glycerol groups; polyethoxylated fatty amines preferably containing 2 to 30 mol of ethylene oxide; oxyethylenated fatty acid esters of sorbitan with 2 to 30 mol of ethylene oxide; fatty acid esters of sucrose, fatty acid esters of polyethylene glycol, alkylpolyglycosides, carbamate or amide derivatives of N-alkylglucamines, aldobionamides, amine oxides such as alkylamine oxides or of N-acylamidopropylmorpholine.

The preferred amphoteric surfactants are secondary or tertiary aliphatic amine derivatives, in which the aliphatic radical is a linear or branched chain containing 8 to 22 carbon atoms and which contains at least one carboxylate, sulphonate, sulphate, phosphate or phosphonate water-solubilizing anionic group; ($C_8$–$C_{20}$)alkylbetaines, sulphobetaines, ($C_8$–$C_{20}$)alkylamido($C_1$–$C_6$)alkylbetaines or ($C_8$–$C_{20}$)alkylamido($C_1$–$C_6$)alkylsulphobetaines.

Among the amine derivatives which may be mentioned are the products sold under the name Miranol, such as those described in U.S. Pat. Nos. 2,528,378 and 2,781,354 and classified in the CTFA dictionary, 7th edition, 1997, under the name Disodium Cocoamphodiacetate, Disodium Lauroamphodiacetate, Disodium Capryloamphodiacetate, Disodium Caproamphodiacetate, Disodium Cocoamphodipropionate, Disodium Lauroamphodipropionate, Disodium Caproamphodipropionate, Disodium Capryloamphodipropionate, Lauroamphodipropionate acid, Cocoamphodipropionate acid.

The cationic surfactants are chosen in particular from optionally polyoxyalkylenated primary, secondary or tertiary fatty amine salts; quaternary ammonium salts; imidazoline derivatives; or amine oxides of cationic nature.

The preferred quaternary ammonium salts are tetraalkylammonium halides (for example chlorides) such as, for example, dialkyldimethylammonium or alkyltrimethylammonium chlorides, in which the alkyl radical contains from about 12 to 22 carbon atoms, in particular behenyltrimethylammonium, distearyldimethylammonium, cetyltrimethylammonium or benzyldimethylstearylammonium chloride or alternatively the stearamidopropyldimethyl (myristyl acetate)ammonium chloride sold under the name <<Cepharyl 70>> by the company Van Dyk.

Diacyloxyethyldimethylammonium, diacyloxyethylhydroxyethylmethylammonium, monoacyloxyethyldihydroxyethylmethylammonium, triacyloxyethylmethylammonium and monoacyloxyethylhydroxyethyldimethylammonium salts (chlorides or methyl sulphate in particular) and mixtures thereof can also be used. The acyl radicals preferably contain 14 to 18 carbon atoms and are more particularly obtained from a plant oil such as palm oil or sunflower oil.

The surfactants are used in the compositions in accordance with the invention in proportions that are sufficient to give the composition a detergent nature, generally in a proportion of at least 4% by weight, preferably between 5% and 50% by weight, relative to the total weight of the composition and in particular between 8% and 35%.

The compositions according to the invention have a pH generally of between 3 and 12 and more particularly between 4 and 8.

The cosmetically acceptable medium for the compositions consists either of water or of one or more solvents or of a mixture of water and at least one solvent chosen from lower alcohols, alkylene glycols and polyol ethers.

The cosmetic performance qualities of the compositions according to the invention can be improved by adding polyorganosiloxanes other than the polyalkylsiloxanes described above and in particular by adding organomodified polyorganosiloxanes. Preferably, silicones containing amine groups, optionally in emulsion form, are then used as organomodified polyorganosiloxanes.

In another preferred embodiment, the compositions of the invention also contain at least one cationic polymer chosen from all those already known per se, in particular those described in patent application EP-A-0 337 354 and in French patent applications FR-A-2 270 846, 2 383 660, 2 598 611, 2 470 596 and 2 519 863.

The cationic polymers used generally have a molecular mass of between 500 and 5 $10^6$ approximately and preferably between $10^3$ and 3 $10^6$ approximately.

Among the cationic polymers which may be mentioned are quaternized proteins (or protein hydrolysates) and polymers of the polyamine, polyaminoamide and polyquaternary ammonium type. These are known products.

The quaternized proteins or protein hydrolysates are in particular chemically modified polypeptides bearing quaternary ammonium groups at the end of a chain, or grafted onto this chain. Their molecular mass can vary, for example, from 1500 to 10,000, and in particular from 2000 to 5000 approximately. Among these compounds, mention may be made in particular of:

collagen hydrolysates bearing triethylammonium groups, such as the products known in the CTFA dictionary as <<Triethonium Hydrolyzed Collagen Ethosulphate>>;

collagen hydrolysates bearing trimethylammonium chloride and trimethylstearylammonium chloride groups, which are known in the CTFA dictionary as <<Steartrimonium Hydrolyzed Collagen>>;

protein hydrolysates bearing on the polypeptide chain quaternary ammonium groups comprising at least one alkyl radical containing from 1 to 18 carbon atoms.

Among these protein hydrolysates which may be mentioned, inter alia, are <<Croquat L>>, <<Croquat M>>, <<Croquat S>> and <Crotein Q>> sold by the company Croda.

Other quaternized proteins or hydrolysates are, for example, those sold by the company Inolex, under the name <<Lexein QX 3000>>.

Mention may also be made of quaternized plant proteins such as wheat, corn or soybean proteins: quaternized wheat proteins which may be mentioned are those known in the CTFA dictionary as <<Cocodimonium Hydrolyzed Wheat Protein>>, <<Lauridimonium Hydrolyzed Wheat Protein>> or <<Steardimonium Hydrolyzed Wheat Protein>>.

The polymers of the polyamine, polyaminoamide or polyquaternary ammonium type which may be used in accordance with the present invention and which may be mentioned in particular are those described in French patents Nos. 2 505 348 and 2 542 997. Among these polymers, mention may be made of:

(1) Quaternized or non-quaternized vinylpyrrolidone/dialkylaminoalkyl acrylate or methacrylate copolymers, such as the polymers described in detail in French patents 2 077 143 and 2 393 573.

(2) Cellulose ether derivatives comprising quaternary ammonium groups, described in French patent 1 492 597.

(3) Cationic cellulose derivatives such as cellulose copolymers or cellulose derivatives grafted with a water-soluble quaternary ammonium monomer, and described in particular in U.S. Pat. No. 4,131,576, such as hydroxyalkylcelluloses, for instance hydroxymethyl-, hydroxyethyl- or hydroxypropylcelluloses grafted in particular with a methacryloylethyltrimethylammonium, methacrylamidopropyltrimethylammonium or dimethyldiallylammonium salt.

(4) Polysaccharides and in particular cationic guar gums described more particularly in U.S. Pat. Nos. 3,589,578 and 4,031,307.

(5) Polymers consisting of piperazinyl units and of divalent alkylene or hydroxyalkylene radicals containing straight or branched chains, optionally interrupted with oxygen, sulphur or nitrogen atoms or with aromatic or heterocyclic rings, as well as the oxidation and/or quaternization products of these polymers. Such polymers are described in particular in French patents 2 162 025 and 2 280 361.

(6) Water-soluble polyaminoamides prepared in particular by polycondensation of an acidic compound with a polyamine; these polyaminoamides can be crosslinked with an epihalohydrin, a diepoxide, a dianhydride, an unsaturated dianhydride, a bis-unsaturated derivative, a bis-halohydrin, a bis-azetidinium, a bis-haloacyldiamine, a bis-alkyl halide or with an oligomer resulting from the reaction of a bifunctional compound which is reactive towards a bis-halohydrin, a bis-azetidinium, a bis-haloacyldiamine, a bis-alkyl halide, an epihalohydrin, a diepoxide or a bis-unsaturated derivative, the crosslinking agent being used in proportions ranging from 0.025 to 0.35 mol per amine group of the polyamlnoamide; these polyaminoamides can be alkylated or, if they comprise one or more tertiary amine functions, they can be quaternized. Such polymers are described in particular in French patents 2 252 840 and 2 368 508.

(7) Polyaminoamide derivatives resulting from the condensation of polyalkylene polyamines with polycarboxylic acids followed by an alkylation with bifunctional agents. Mention may be made, for example, of adipic acid/dialkylaminohydroxyalkyldialkylenetriamine polymers in which the alkyl radical contains from 1 to 4 carbon atoms and preferably denotes methyl, ethyl or propyl. Such polymers are described in particular in French patent 1 583 363.

(8) Polymers obtained by reacting a polyalkylene polyamine comprising two primary amine groups and at least one secondary amine group with a dicarboxylic acid chosen from diglycolic acid and saturated aliphatic dicarboxylic acids containing from 3 to 8 carbon atoms, the molar ratio between the polyalkylene polyamine and the dicarboxylic acid being between 0.8:1 and 1.4:1, the polyaminoamide resulting therefrom being reacted with the epichlorohydrin in a molar ratio of epichlorohydrin relative to the secondary amine group of the polyaminoamide of between 0.5:1 and 1.8:1. Such polymers are described in particular in U.S. Pat. Nos. 3,227,615 and 2,961,347.

(9) Cyclopolymers of methyldiallylamine or of dimethyidiallylammonium, in particular those described in French patent 2 080 759 and in its Certificate of Addition 2 190 406.

(10) The diquaternary ammonium polymers described in French patents 2 320 330, 2 270 846, 2 316 271, 2 336 431 and 2 413 907 and U.S. Pat. Nos. 2,273,780, 2,375,853, 2,388,614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945 and 4,027,020.

(11) The polyquaternary ammonium polymers described in particular in patent application EP-A-122 324.

(12) Homopolymers or copolymers derived from acrylic or methacrylic acids and comprising $CH_2$—$CHR_a$—CO—O—$A_1$—$NR_eR_f$, $CH_2$—$CHR_a$—CO—O—$A_1$—$N^+R_bR_cR_d$, $X^-$ and/or $CH_2$—$CHR_a$—CO—NH—$A_1$—$N^+R_bR_cR_d$, $X^-$ units, in which the groups $R_a$ independently denote H or $CH_3$, the groups $A_1$, independently denote a linear or branched alkyl group of 1 to 6 carbon atoms or a hydroxyalkyl group of 1 to 4 carbon atoms, the groups $R_b$, $R_c$ and $R_d$, which may be identical or different, independently denote an alkyl group of 1 to 18 carbon atoms or a benzyl radical, the groups $R_e$ and $R_f$ represent a hydrogen atom or an alkyl group of 1 to 6 carbon atoms, $X^-$ denotes an anion, for example methosulphate or halide, such as chloride or bromide.

(13) Quaternary polymers of vinylpyrrolidone and of vinylimidazole such as, for example, the products sold under the names <<Luviquat FC 905>>, <<Luviquat FC 550>> and <<Luviquat FC 370>> by the company BASF.

(14) The polyamines such as <<Polyquart H>> sold by Henkel, referred to under the name <<Polyethylene Glycol Tallow Polyamine>> in the CTFA dictionary.

(15) Crosslinked polymers of methacryloyloxyethyltrimethylammonium salts, such as the polymers obtained by homopolymerization of dimethylaminoethyl methacrylate quaternized with methyl chloride, or by copolymerization of acrylamide with dimethylaminoethyl methacrylate quaternized with methyl chloride, the homo- or copolymerization being followed by a crosslinking with a compound containing olefinic unsaturation, in particular methylenebisacrylamide. An acrylamide/methacryloyloxyethyltrimethylammonium chloride crosslinked copolymer (20/80 by weight) in the form of a dispersion containing 50% by weight of the said copolymer in mineral oil can more particularly be used.

Other cationic polymers which can be used in the context of the invention are polyalkyleneimines, in particular polyethyleneimines, polymers containing vinylpyridine or vinylpyridinium units, condensates of polyamines and of epichlorohydrin, polyquaternary ureylenes and chitin derivatives.

Among the cationic polymers which can be used in the context of the present invention, cellulose ether derivatives comprising quaternary ammonium groups, polysaccharides and in particular cationic guar gums and cyclopolymers of methyldiallylamine or of dimethyldiallylammonium are preferred.

The cationic polymers are used in the compositions of the invention in proportions of between 0.001% and 20% by weight and preferably between 0.05% and 5% by weight, relative to the total weight of the composition.

The compositions according to the invention can furthermore also contain at least one adjuvant chosen from the adjuvants usually used in cosmetics, such as fragrances, preserving agents, sequestering agents, wetting agents, sugars, plant, animal, mineral or synthetic oils, amphoteric polymers, menthol, nicotinate derivatives, agents for preventing hair loss, antidandruff agents, screening agents, foam stabilizers, propellants, dyes, ceramides, vitamins or provitamins, acidifying or basifying agents or other well-known cosmetic adjuvants.

In one preferred embodiment of the invention, the compositions according to the invention are used as shampoos for washing the hair.

The process for washing keratin materials consists in applying a composition as defined above to wet or dry keratin materials in amounts that are effective to wash them, this application being followed by rinsing after an optional period of leaving the composition to stand on the keratin materials.

The examples which follow are intended to illustrate the invention.

EXAMPLE 1

Shampoo

| | |
|---|---|
| Propylene glycol | 0.1 g |
| Cocoyl betaine as an aqueous 30% solution | 8 g |
| Hydroxypropyl guar trimethylammonium chloride sold under the name <<Jaguar C 13S>> by the company Meyhall | 0.05 g |
| Polydimethylsiloxane with a viscosity of 0.3 $m^2.s^{-1}$, sold under the name DC 200/300,000 by the company Dow Corning | 2.7 g |
| 1-(Hexadecyloxy)-2-octadecanol/cetyl alcohol mixture | 2.5 g |
| Fragrance | 0.5 g |
| Coconut acid monoisopropanolamide | 0.5 g |
| Sodium lauryl ether sulphate (2.2 EO) containing 70% A.M. | 22 g |
| Terpolymer af acrylates, amino(meth)acrylates and $C_{10}$–$C_{30}$ alkyl itaconate, polyoxyethylenated with 20 mol of ethylene oxide, as an aqueous dispersion containing 20% A.M., sold under the name <<Structure ® Plus>> by the company National Starch | 1 g |
| Citric acid | 0.05 g |
| Preserving agents | qs |
| Sterilized demineralized water | qs 100 g |

The pH is adjusted to 7.5 with citric acid or with sodium hydroxide. After using this shampoo, it is found that the dried hair has suppleness, manageability and body. The hair is easy to disentangle and looks smooth.

EXAMPLE II

Shampoo

| | |
|---|---|
| Propylene giycoi | 0.1 g |
| Cocoyl betaine as an aqueous 30% solution | 8 g |
| Hydroxypropyl guar trimethylammonium chloride sold hy the company Meyhall under the name <<Jaguar C 13S>> | 0.2 g |
| Polydimethylsiloxane with a viscosity of 0.3 $m^2.s^{-1}$ sold under the name AK. 300,000 by the company Wacker | 2.7 g |
| 1-(Hexadecyloxy)-2-octadecanol/cetyl alcohol mixture | 2.5 g |
| Coconut acid monoisopropanolamide | 0.5 g |
| Sodium lauryl ether sulphate (2.2 EO) containing 70% A.M. | 22.25 g |
| Terpolymer of acrylates, amino(meth)acrylates and $C_{10}$–$C_{30}$ alkyl itaconate, polyoxyethylenated with 20 mol of ethylene oxide, as an aqueous dispersion containing 20% A.M., sold under the name <<Structure ® Plus>> by the company National Starch | 1 g |
| Preserving agents, fragrance | qs 0.05 g |
| Citric acid | 100 g |
| Sterilized demineralized water | qs |

The pH is adjusted to 7.5 with citric acid or with sodium hydroxide. After using this shampoo, it is found that the dried hair has suppleness, manageability and body. The hair is easy to disentangle and looks smooth.

EXAMPLE III

Shampoo

| | |
|---|---|
| Sodium chloride | 0.3 g |
| Vitamin B3 or PP: nicotinamide | qs |
| Scdium N-cocoylamidoethyl-N-ethoxycarboxymethyl glycinate (38%) | 1.5 g |
| Vitamin B6: pyridoxine hydrochioride | qs |
| Hydroxypropyl guar trimethylammonium chloride sold under the name <<Jaguar C 13S>> by the company Meyhall | 0.04 g |
| Polydimethylsiloxane with a viscosity of 0.3 $m^2.s^{-1}$ sold under the name DC 200/300,000 by the company Dow Corning | 1.8 g |
| Oxyethylenated lauryl alcohol (2.5 EO) | 0.75 g |
| Extract of fruits in aqueous solution | qs |
| Coconut acid monoisopropanolamide | 2 g |
| Cocoylamidopropylbetaine as an aqueous 38% solution | 2.7 g |
| Sodium lauryl ether sulphate (2.2 EO) at 70% | 17 g |
| Pyrus Malus (INCI) | qs |
| Distearyl ether | 1.5 g |
| Terpolymer of acrylates, amino(meth)acrylates and $C_{10}$–$C_{30}$ alkyl itaconate, poiyoxyethylenated with 20 mol of ethylene oxide, as an aqueous dispersion containing 20% A.M., sold under the name <<Structure ® Plus>> by the company National Starch | 1 g |
| Mixture of linear alcohols (C18/C20/C22) | 1.5 g |
| Fragrance, preserving agents | qs |
| Sterilized demineralized water | qs 100 g |

The pH is adjusted to 7.5 with citric acid or with sodium hydroxide. After using this shampoo, it is found that the dried hair has suppleness, manageability and body. The hair is easy to disentangle and looks smooth.

We claim:

1. A composition for washing keratin materials, comprising, in a cosmetically acceptable medium,
   at least one detergent surfactant,
   at least one polyorganosiloxane oil with a viscosity greater than or equal to 0.1 $m^2.s^{-1}$, and
   at least one acrylic terpolymer containing, in amounts based on the total weight of monomers constituting the terpolymer:
   acrylate monomer (a), in amount of 5% to 80% by weight and selected from the group consisting of a $C_1$–$C_6$ alkyl acrylate and a $C_1$–$C_6$ alkyl methacrylate;

monomer (b), in an amount of 5% to 80% by weight and selected from the group consisting of a heterocyclic vinyl compound containing at least one nitrogen or sulphur atom, a (meth)acrylamide, a mono- and di($C_1$–$C_4$)alkylamino($C_1$–$C_4$)alkyl (meth) acrylate, and a mono- and di($C_1$–$C_4$)alkylamino ($C_1$–$C_4$)alkyl(meth)acrylamide; and monomer (c), in an amount of 0.1% to 30% by weight and selected from the group consisting of:
- i) a urethane produced by reaction between a monoethylenic unsaturated isocyanate and a nonionic surfactant encompassing a block copolymer of 1,2-butylene oxide and of ethylene oxide containing a $C_{1-4}$ alkoxy end;
- ii) a copolymerizable ethylenic unsaturated surfactant monomer obtained by condensing a nonionic surfactant with an α,β-ethylenic unsaturated carboxylic acid or its anhydride;
- iii) a urea surfactant monomer produced by reacting a monoethylenic unsaturated monoisocyanate with a nonionic surfactant containing an amine functionality;
- iv) a (meth)allyl ether of formula $CH_2=CR_1CH_2OA_mB_nA_pR_2$ in which $R_1$ denotes a hydrogen atom or a methyl group, A denotes a propylenoxy or butylenoxy group, B denotes ethylenoxy, n is equal to zero or denotes an integer less than or equal to 200, m and p denote zero or an integer less than n, and $R_2$ is a hydrophobic group of at least 8 carbon atoms; and
- v) a nonionic urethane monomer produced by reacting a monohydric nonionic surfactant with a monoethylenic unsaturated isocyanate.

2. The composition according to claim 1, wherein the terpolymer is present in a proportion of 0.01% to 20% by weight relative to the total weight of the composition.

3. The composition according to claim 1, wherein the acrylate monomer (a) is a $C_2$–$C_6$ alkyl acrylate.

4. The composition according to claim 1, wherein the monomer (b) is N,N-dimethylaminoethyl methacrylate, N,N-diethylaminoethyl acrylate, N,N-diethylaminoethyl methacrylate, N-t-butylaminoethyl acrylate, N-t-butylaminoethyl, methacrylate, N,N-dimethylaminopropylacrylamide, N,N-dimethylaminopropylmethacrylamide, N,N-diethylaminopropylacrylamide, or N,N-diethylaminopropyl-methacrylamide.

5. The composition according to claim 1, wherein the monomer (c) is a copolymerizable ethylenic unsaturated surfactant monomer obtained by condensing a nonionic surfactant with itaconic acid.

6. The composition according to claim 1, wherein the acrylic terpolymer consists of acrylates, amino (meth)acrylates, and $C_{10}$–$C_{30}$ alkyl itaconate polyoxyethylenated with 20 mol of ethylene oxide.

7. The composition according to claim 1, said acrylic terpolymer further containing a crosslinking monomer.

8. The composition according to claim 1, wherein the polyorganosiloxane oil with a viscosity greater than or equal to $0.1\ m^2.s^{-1}$ is:
- i) a polyalkylsiloxane;
- ii) a polyarylsiloxane;
- iii) a polyalkylarylsiloxane;
- iv) a silicone gum;
- v) a silicone resin; or
- vi) a mixture thereof.

9. The composition according to claim 8, wherein the polyorganosiloxane oil with a viscosity greater than or equal to $0.1\ m^2.s^{-1}$ is a polyalkylsiloxane or a silicone gum.

10. The composition according to claim 1, wherein the polyorganosiloxane oil with a viscosity greater than or equal to $0.1\ m^2.s^{-1}$ is present in a proportion of 0.01% to 20% by weight relative to the total weight of the composition.

11. The composition according to claim 1, wherein the detergent surfactant is selected from the group consisting of anionic, amphoteric, nonionic, and cationic surfactants and mixtures thereof.

12. The composition according to claim 11, wherein the anionic surfactants are selected from the group consisting of alkaline salts, magnesium salts, ammonium salts, amine salts, and amino alcohol salts of:
- alkyl sulphates, alkyl ether sulphates, alkylamido ether sulphates, alkylaryl polyether sulphates, monoglyceride sulphates, alkyl sulphonates, alkylamide sulphonates, alkylaryl sulphonates, olefin sulphonates, paraffin sulphonates, alkyl sulphosuccinates, alkyl ether sulphosuccinates, alkylamide sulphosuccinates, alkyl sulphosuccinamates, alkyl sulphoacetates, alkyl phosphates, alkyl ether phosphates, acyl sarcosinates, acyl isethionates, or N-acyl taurates,
  - wherein alkyl and acyl is a carbon-based chain containing from 8 to 30 carbon atoms;
- fatty acid salts of oleic, ricinoleic, palmitic, or stearic acid; coconut oil acid or hydrogenated coconut oil acid; acyl lactylates, in which the acyl radical contains from 8 to 30 carbon atoms; alkyl D-galactosiduronic acids or salts thereof, polyoxyalkylenated carboxylic alkyl or alkylaryl ether acids or salts thereof, or polyoxyalkylenated carboxylic alkylamido ether acids or salts thereof.

13. The composition according to claim 11, wherein the nonionic surfactants are: polyethoxylated, polypropoxylated, or polyglycerolated fatty acids, alkylphenols, or alcohols having a fatty chain containing 8 to 30 carbon atoms, having between 2 and 50 ethylene oxide or propylene oxide groups, and having 2 and 30 glycerol groups; copolymers of ethylene oxide or of propylene oxide; condensates of ethylene oxide or of propylene oxide with fatty alcohols; polyethoxylated fatty amides; polyglycerolated fatty amides; polyethoxylated fatty amines; oxyethylenated fatty acid esters of sorbitan; fatty acid esters of sucrose or fatty acid esters of polyethylene glycol; alkylpolyglycosides; amide or carbamate derivatives of N-alkylglucamines, aldobionamides, or amine oxides.

14. The composition according to claim 11, wherein the amphoteric surfactants are: secondary or tertiary aliphatic amine derivatives, in which the aliphatic radical is a linear or branched chain containing from 8 to 22 carbon atoms and which contains at least one carboxylate, sulphonate, sulphate, phosphate or phosphonate water-solubilizing anionic group; ($C_8$–$C_{20}$)alkylbetaines, sulphobetaines, ($C_8$–$C_{20}$) alkyl amido($C_1$–$C_6$)alkylbetaines or ($C_8$–$C_{20}$) alkylamido ($C_1$–$C_6$)alkylsulphobetaines.

15. The composition according to claim 11, wherein the cationic surfactants are: optionally polyoxyalkylenated, primary, secondary or tertiary fatty amine salts; quaternary ammonium salts; imidazoline derivatives; or cationic amine oxides.

16. The composition according to claim 1, wherein the detergent surfactant is present in a proportion of at least 4% by weight relative to the total weight of the composition.

17. The composition according to claim 1, having a pH between 3 and 12.

18. The composition according to claim 1, wherein the cosmetically acceptable medium is water, one or more solvents, or of a mixture of water and at least one solvent selected from the group consisting of lower alcohols, alkylene glycols, and polyol ethers.

19. The composition according to claim 1, further comprising at least one organomodified polyorganosiloxane.

20. The composition according to claim 1, further comprising at least one cationic polymer selected from the group consisting of:
   proteins and protein hydrolysates,
   polyamine, polyaminoamide, and polyquaternary ammonium polymers, and
   polyalkyleneimines, polymers containing vinylpyridine or vinylpyridinium units, condensates of polyamines and of epichlorohydrin, polyquaternary ureylenes, and chitin derivatives.

21. The composition according to claim 20, wherein the cationic polymer is present in a proportion between 0.001% and 20% by weight relative to the total weight of the composition.

22. The composition according to claim 1, further comprising at least one cosmetically acceptable adjuvant selected from the group consisting of fragrances, preserving agents, sequestering agents, wetting agents, sugars, plant oils, animal oils, synthetic oils, amphoteric polymers, menthol, nicotinate derivatives, agents for preventing hair loss, antidandruff agents, foam stabilizers, propellants, dyes, ceramides, vitamins, provitamins, acidifying agents, and basifying agents.

23. In a shampoo, the improvement wherein the shampoo contains the composition as defined in claim 1.

24. A process for washing keratin materials, comprising the step of applying to the keratin materials, wet or dry, at least one composition as defined in claim 1.

25. The process according to claim 24, further comprising the step of rinsing the keratin materials with water after the applying step.

26. The process according to claim 25, further comprising the step of leaving the composition on the keratin materials for a period of time before the rinsing step.

27. The composition of claim 1, wherein monomer (a) is present in an amount of 15% to 70% by weight.

28. The composition of claim 1, wherein monomer (a) is present in an amount of 40% to 70% by weight.

29. The composition of claim 1, wherein monomer (b) is present in an amount of 10% to 70% by weight.

30. The composition of claim 1, wherein monomer (b) is present in an amount of 20% to 60% by weight.

31. The composition of claim 1, wherein monomer (c) is present in an amount of 0.1% to 10% by weight.

32. The composition of claim 2, wherein the terpolymer is present in a proportion of 0.1% to 10% by weight relative to the total weight of the composition.

33. The composition of claim 3, wherein the monomer (a) is ethyl acrylate.

34. The composition of claim 4, wherein the monomer (b) is N,N-dimethylaminoethyl methacrylate.

35. The composition according to claim 10, wherein the polyorganosiloxane oil with a viscosity greater than or equal to 0.1 $m^2 \cdot s^{-1}$ is present in a proportion of 0.1% to 10% by weight relative to the total weight of the composition.

36. The composition according to claim 16, wherein the detergent surfactant is present in a proportion of 5% to 50% by weight relative to the total weight of the composition.

37. The composition according to claim 19, wherein the organomodified polyorganosiloxane is an aminated polyorganosiloxane.

38. The composition according to claim 20, wherein:
   the protein hydrolysates are collagen hydrolysates bearing triethylammonium groups, collagen hydrolysates bearing trimethylammonium chloride and trimethylstearylammonium chloride groups, protein hydrolysates bearing on the polypeptide chain quaternary ammonium groups comprising at least one alkyl radical containing from 1 to 18 carbon atoms, or quaternized plant proteins; and
   the polyamine, polyaminoamide, or polyquaternary ammonium polymers are
   i) quaternized or non-quaternized vinylpyrrolidone/dialkylaminoalkyl acrylate or methacrylate copolymers,
   ii) cellulose ether derivatives comprising quaternary ammonium groups,
   iii) cationic cellulose derivatives,
   iv) polysaccharides,
   v) polymers consisting of piperazinyl units and of divalent alkylene or hydroxyalkylene radicals containing straight or branched chains, optionally interrupted with oxygen, sulphur, or nitrogen atoms or with aromatic or heterocyclic rings, or oxidation or quaternization products of said polymers,
   vi) water-soluble polyaminoamides,
   vii) polyaminoamide derivatives,
   viii) polymers obtained by reacting a polyalkylene polyamine comprising two primary amine groups and at least one secondary amine group with a dicarboxylic acid selected from the group consisting of diglycolic acid and saturated aliphatic dicarboxylic acids containing from 3 to 8 carbon atoms,
   ix) cyclopolymers of methyldiallylamine or of dimethyldiallylammonium,
   x) diquaternary ammonium polymers,
   xi) polyquaternary ammonium polymers,
   xii) homopolymers or copolymers derived from acrylic or methacrylic acids and comprising
   $CH_2$—$CHR_a$—CO—O—$A_1$—$NR_eR_f$, $CH_2$—$CHR_a$CO—O—$A_1$—$N^+R_bR_cR_d$ $X^-$, and/or $CH_2$—$CHR_a$—CO—NH—$A_1$—$N^+R_bR_cR_d$ $X^-$ units,
      in which $R_a$ independently denotes H or $CH_3$, $A_1$ independently denotes linear or branched alkyl of 1 to 6 carbon atoms or hydroxyalkyl of 1 to 4 carbon atoms, $R_b$, $R_c$ and $R_d$, which are identical or different, independently denote alkyl group of 1 to 18 carbon atoms or benzyl, $R_e$ and $R_f$ represent a hydrogen atom or alkyl of 1 to 6 carbon atoms, and $X^-$ denotes an anion,
   xiii) quaternary polymers of vinylpyrrolidone or of vinylimidazole,
   xiv) polyethylene glycol tallow polyamine, or
   xv) crosslinked polymers of methacryloyloxyethyltrimethylammonium chloride.